United States Patent
Seethamraju (10) Patent No.: US 10,346,586 B2
(45) Date of Patent: Jul. 9, 2019

(54) PROTOCOL MANAGEMENT SYSTEM (PROMS)

(71) Applicant: Siemens Healthcare GmbH, Erlangen OT (DE)

(72) Inventor: Ravi Teja Seethamraju, Malden, MA (US)

(73) Assignee: Siemens Healthcare GmbH, Erlangen (DE)

( * ) Notice: Subject to any disclaimer, the term of this patent is extended or adjusted under 35 U.S.C. 154(b) by 1128 days.

(21) Appl. No.: 14/296,536

(22) Filed: Jun. 5, 2014

(65) Prior Publication Data

US 2015/0356244 A1    Dec. 10, 2015

(51) Int. Cl.
  *G06F 19/00*   (2018.01)
  *G06F 16/51*   (2019.01)
  *H04N 1/32*    (2006.01)
  *G16H 40/63*   (2018.01)

(52) U.S. Cl.
  CPC ............ *G06F 19/321* (2013.01); *G06F 16/51* (2019.01); *H04N 1/32512* (2013.01); *G16H 40/63* (2018.01)

(58) Field of Classification Search
  None
  See application file for complete search history.

(56) References Cited

U.S. PATENT DOCUMENTS

| 2004/0143582 | A1* | 7/2004 | Vu ..................... G06F 17/30961 |
| 2004/0148403 | A1* | 7/2004 | Choubey ............... G06F 19/325 709/228 |
| 2005/0234325 | A1  | 10/2005 | Hofmann et al. |
| 2007/0211756 | A1* | 9/2007 | Glaser-Seidnitzer ........ A61B 5/055 370/466 |

(Continued)

FOREIGN PATENT DOCUMENTS

| CN | 103647830 A | 3/2014 |
| WO | 2013049818 A1 | 4/2013 |

OTHER PUBLICATIONS

European Search Report, EP Patent Application No. 15169714.1, dated Nov. 17, 2015, 6 pages.

(Continued)

*Primary Examiner* — Lena Najarian (57) ABSTRACT

A computer-implemented method for managing imaging protocols among a plurality of image scanners includes creating parent node data records, each respective parent node data record corresponding to a distinct type of image scanner. Imaging protocols are stored, each imaging protocol associated with a distinct parent node data record included in the parent node data records. Next, a child node creation process is performed for each respective image scanner. The child node creation process may include, for example: determining a respective image scanner type associated with a respective image scanner; identifying a respective parent node data record corresponding to the respective (Continued)

image scanner type; creating a child node data record associated with the respective parent node data record; identifying a respective imaging protocol associated with the respective parent node; and storing a copy of the respective imaging protocol at the respective scanner.

12 Claims, 6 Drawing Sheets

(56) References Cited

U.S. PATENT DOCUMENTS

| | | | |
|---|---|---|---|
| 2011/0110568 A1* | 5/2011 | Vesper | G06F 19/321 |
| | | | 382/128 |
| 2012/0041909 A1 | 2/2012 | Glaser-Seidnitzer et al. | |
| 2013/0132777 A1* | 5/2013 | Froehlich | G06F 11/3688 |
| | | | 714/37 |

OTHER PUBLICATIONS

Radiology protocols, Instant access to the world's first protocol management platform, https://www.radiologyprotocols.com, webpage, 4 pages, printed Jun. 5, 2014.

IBM Rational ClearCase, http://www-03.ibm.com/software/products/en/clearcase, webpage, 3 pages, printed Jun. 5, 2014.

CN office action in application No. 201510292361.2, dated May 2, 2018, 27 pages (English translation attached).

* cited by examiner

PROTOCOL MANAGEMENT SYSTEM (PROMS)

TECHNICAL FIELD

The present invention relates generally to methods, systems, and apparatuses for managing imaging protocols across a group of image scanner devices. The disclosed methods, systems, and apparatuses may be applied to, for example, imaging modalities such as Magnetic Resonance Imaging (MRI).

BACKGROUND

Magnetic Resonance Imaging (MRI) is a non-invasive medical imaging technique that utilizes magnetization to visualize soft tissue. The contrast of MRI is extraordinarily flexible; several physical tissue properties can be used as contrast parameters to extract anatomical, morphological and even functional information. Tissue properties may include but are not limited to relaxation parameters, diffusion perfusion, flow, etc. The achieved image contrast strongly depends on the used Magnetic Resonance (MR) protocols—a specific set of imaging parameters that describe data acquisition and image reconstruction. Such imaging protocols are the core element of a clinical MRI study. The optimal selection of an imaging protocol and associated imaging parameters strongly impacts the image quality and diagnostic performance of the MRI study and requires careful optimization to specific types of MRI scanners. Unfortunately, even small deviations from optimized MRI protocols may render an MR image as non-diagnostic, resulting in repeated scans or even call backs of the patients.

Accordingly, in institutions that deploy more than one image scanner, there is a need to harmonize imaging protocols across the scanners for the sake of uniformity and consistency. However, currently such harmonization can only be achieved, at best, semi-automatically. For example, on some conventional scanners, it is possible to manually export a protocol from one scanner and import on another or to transfer a protocol via Digital Imaging and Communications in Medicine (DICOM) transfer. The protocol must then be manually imported onto another scanner. Moreover, it is challenging to transfer protocols between individual scanners due to configuration differences that may exist between different scanners. For example, in the case of MRI, scanner differences can exist due to factors such as field strength and gradient performance. Although, it is possible to transfer a protocol from a scanner with one configuration to a scanner with a different configuration, the importing system is required to make changes to the protocol during the importing process based on certain heuristic rules which may introduce errors in the imported data.

Additionally, conventional techniques for storing imaging protocols are suboptimal. For example, imaging protocols are typically stored locally on the hard disk of the scanner, so in the event of a system crash, accidental deletion or modification, these protocols are irreversibly lost. While it is possible to create manual backups of the protocols at regular intervals, these backups are complete backups requiring large memory foot print and considerable amount of time to restore.

Accordingly, it is desired to provide an imaging protocol management system to allow for coordination, storage, and maintenance of imaging protocols across a group of image scanners.

SUMMARY

Embodiments of the present invention address and overcome one or more of the above shortcomings and drawbacks, by providing methods, systems, and apparatuses that allow for management of imaging protocols using a node-based system. More specifically, a parent node is created and used to represent a type of image scanner. Then, one or more child nodes of this parent node are created and used to represent actual image scanners of that type. This technology is particularly well-suited for, but by no means limited to, imaging modalities such as Magnetic Resonance Imaging (MRI).

According to some embodiments of the present invention, a computer-implemented method for managing imaging protocols among a plurality of image scanners is performed by creating a plurality of parent node data records, each respective parent node data records corresponding to a distinct type of image scanner. A plurality of imaging protocols is stored, with each imaging protocol associated with a distinct parent node data record. Next, a child node creation process is performed for each respective image scanner. In one embodiment, this child node creation process includes determining a respective image scanner type associated with a respective image scanner and identifying a respective parent node data record corresponding to the respective image scanner type. Next, a child node data record associated with the respective parent node data record is created and the imaging protocol associated with the respective parent node is identified. Then, a copy of the respective imaging protocol is stored at the respective scanner. In some embodiments, a virtual copy is stored at the scanner rather than a full version of the file containing the imaging protocol.

In some embodiments, the aforementioned method may include additional features to handle modifications of imaging protocols. For example, in one embodiment the aforementioned method also includes detecting a modification of an imaging protocol at an image scanner. Based on this detection, a child node data record corresponding to the image scanner is identified and used to determine a parent node data record. Next, one or more additional child node data records associated with the parent node data record are determined. Then, the modification of the imaging protocol is distributed to one or more additional image scanners associated with the additional child node data records. In some embodiments, the modification is stored with an association to the parent node data record. Prior to storing the modification, the original imaging protocol may be archived.

In some embodiments, process of handling modifications may be extended with additional functionality to handle data merging between different types of image scanners. For example, in one embodiment, a second imaging protocol associated with a second parent node data record is identified and the modification of the imaging protocol discussed above is merged into the second imaging protocol to yield an updated second imaging protocol. Next, child node data records associated with the second parent node data record are identified and used to determine which image scanners should receive the updated second imaging protocol. Prior to distributing the updated second imaging protocol, a notification may be provided to an administrator describing the updated second imaging protocol. In some embodiments, updated second imaging protocol is only distributed to the image scanners if an approval is received from the administrator in response to the notification. Additionally, the method may be adapted to handle modifications from the administrator. For example, in one embodiment, additional modifications are received from the administrator in response to the notification. These modifications may then be merged into the updated second imaging protocol prior to distributing the updated second imaging protocol to the one or more second image scanners.

According to other embodiments of the present invention, a computer-implemented method for managing imaging protocols among a plurality of image scanners includes identifying a grouping of image scanners comprising one or more image scanners of a distinct type and assigning a distinct imaging protocol to the grouping. Next, a copy (or virtual copy) of the distinct imaging protocol is stored at each image scanner in the grouping. When a modification of the copy by an image scanner is detected, that modification is distributed to each image scanner included in the grouping. In some embodiments, this modification may also be merged with imaging protocols associated with other groupings of scanners. The merged imaging protocol may then be distributed to those other groupings, for example immediately or following approval from an administrator.

Various articles, systems, and apparatuses may be used to implement the aforementioned methods. For example, in some embodiments, an article of manufacture for managing imaging protocols among a plurality of image scanners includes a non-transitory, tangible computer-readable medium holding computer-executable instructions for performing the methods discussed above.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

The present invention relates generally to methods, systems, and apparatuses for managing imaging protocols used by an organization such as a hospital. The various embodiments described herein offer several benefits to the organization. For example, using the techniques described herein, a node-based system is used to group image scanners by type. These groupings may then be used to optimize management tasks such as, for example, processing and distributing updates to imaging protocols. In some embodiments, the node-based system stores imaging protocols in a centralized repository. Such a centralized repository of imaging protocols will help to improve reproducibility and consistency of images across sites and departments associated with the organization. In turn, this may help to reduce certain costs associated with performing imaging. The disclosed methods, systems, and apparatuses may be applied to, for example, imaging modalities such as Magnetic Resonance Imaging (MRI).

Figure 1:
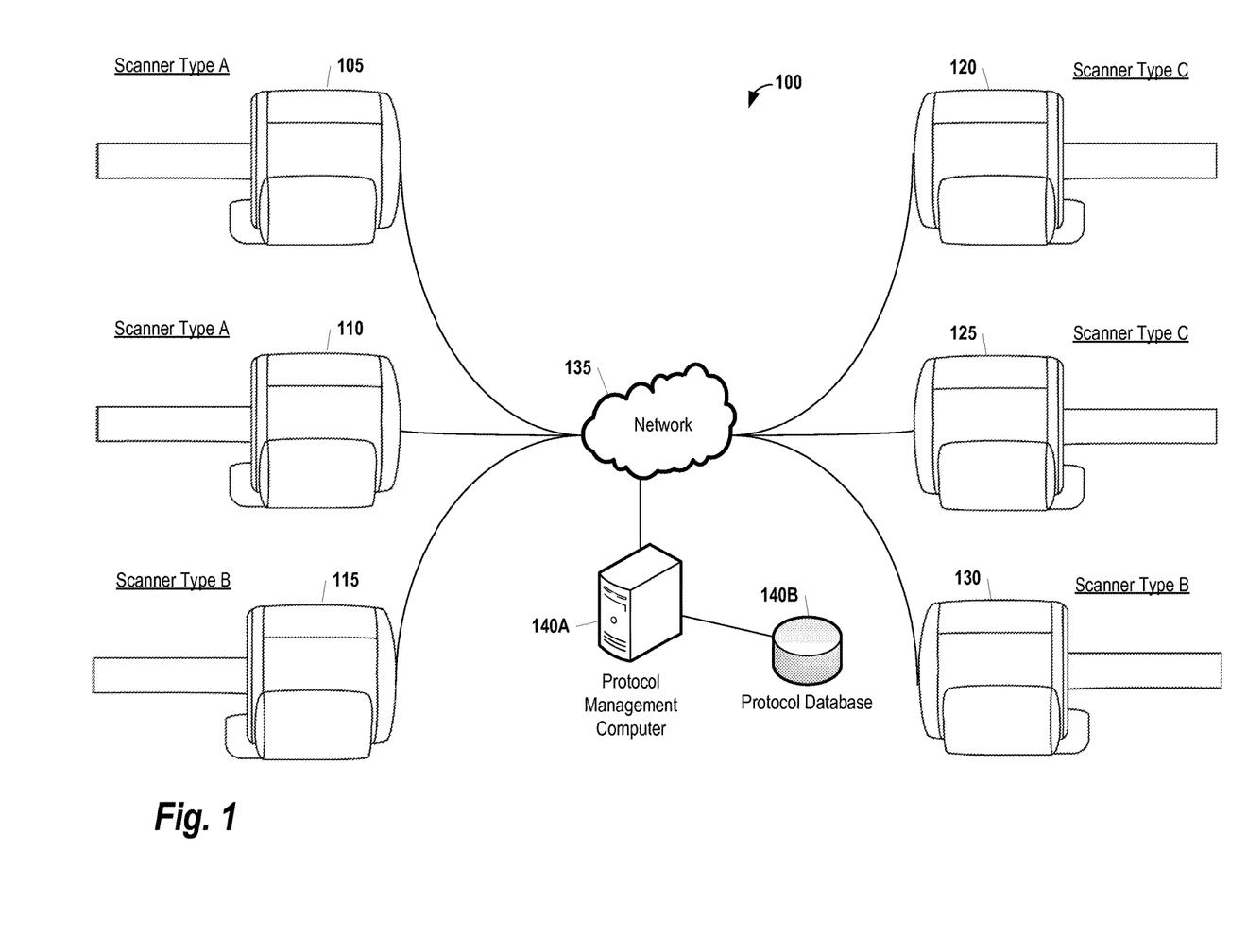
FIG. 1 shown a system for coordinating the sharing and storage of imaging protocols across a group of image scanners.

FIG. 1 shows a system 100 for coordinating the sharing and storage of imaging protocols across a group of image scanners, according to some embodiments of the present invention. In the example of FIG. 1, imaging devices image scanners 105, 110, 115, 120, 125, and 130 are each depicted as MRI device. In this instance, the imaging protocol utilized by each scanner may include information such as, without limitation, repetition time (TR), echo time (TE), spatial and temporal resolution, and/or inversion times (TI). It should also be understood that the use of MRI devices in FIG. 1 is only one example of the types of imaging modalities which may be integrated with the methods, systems, and apparatuses described herein. In other embodiments, different imaging devices may be used with different corresponding protocols.

Image scanners 105, 110, 115, 120, 125, and 130 are each connected (either directly or indirectly) to a Protocol Management Computer 140A via a network 135. The Protocol Management Computer 140A includes a Protocol Database 140B storing one or more imaging protocols. In some embodiments, the Protocol Management Computer 140A and/or the Protocol Database 140B may include various redundancy and other failover features. The imaging protocols stored in the Protocol Database 140B may include standard imaging protocols (e.g., Society for Cardiovascular Magnetic Resonance protocols) as well as modifications to the standard imaging protocols. The Protocol Management Computer 140A further stores identifying information about each type of scanner connected to it via the network 135. Thus, in the example of FIG. 1, the Protocol Management Computer 140A stores information which identifies image scanners 105 and 110 as Type A, image scanners 115 and 130 as Type B, and image scanners 120 and 125 as Type C. The identifying information stored about each type of image scanner may include, for example, information regarding the make and model of the scanner, the version of software executed by the scanner, or various other hardware and/or software configuration information. Additionally, in some embodiments, the identifying information further includes organizational specific information such as the location of the image scanner, a list of authorized users of the image scanners, or a history of past uses of the image scanner.

Through interaction with the Protocol Management Computer 140A, the image scanners 105, 110, 115, 120, 125, and 130 are able to view, download, use, and request modifications to the imaging protocols stored in the Protocol Database 140B. In some embodiments, the Protocol Management Computer 140A stores and maintains all standard protocols, along with any proposed modifications, in a version control system. In such a system, each the image protocol associated with scanner type may be stored as a "version" of an original, standard protocol.

Figure 2:
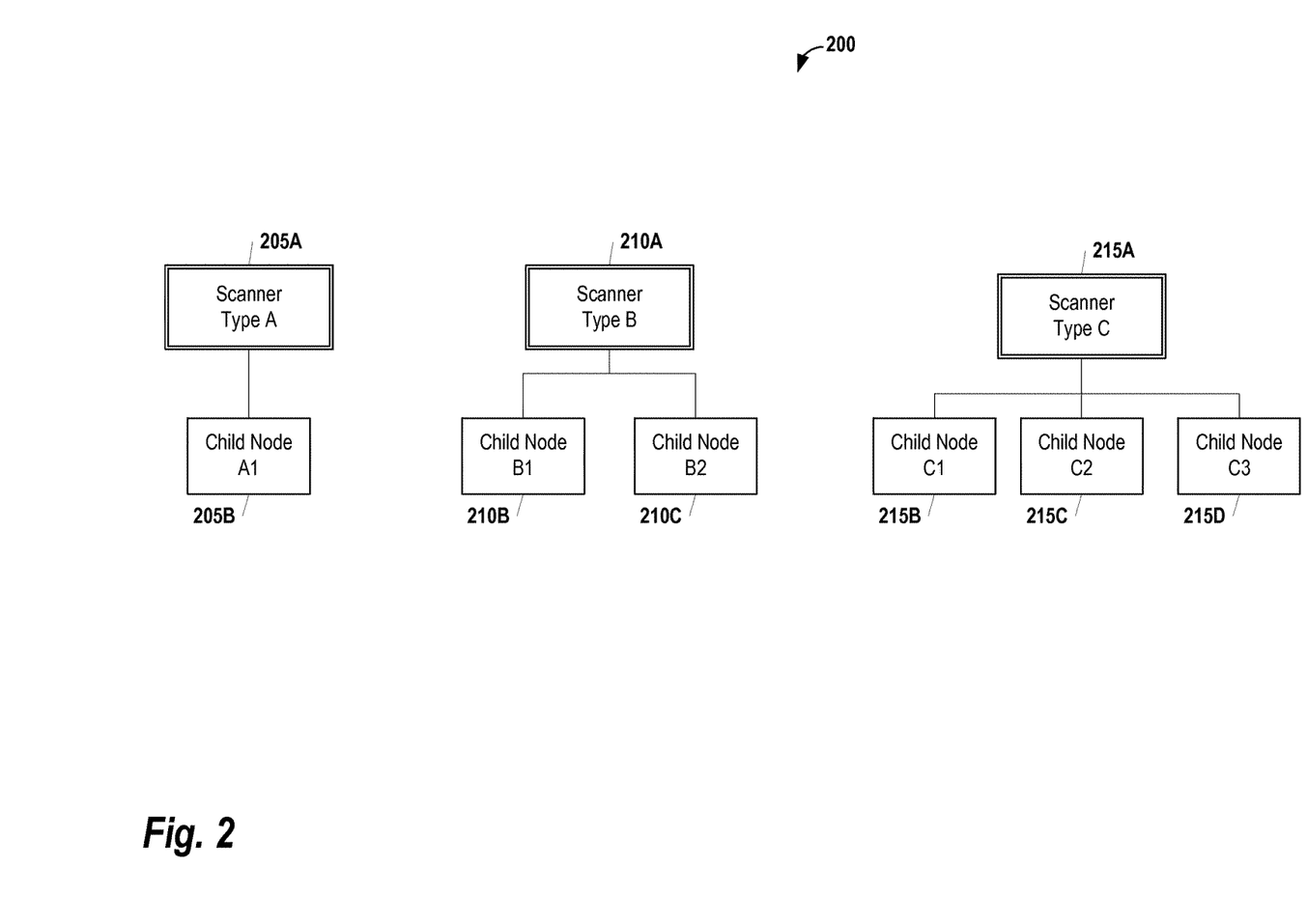
FIG. 2 provides an example of how image scanners may be grouped, according to some embodiments of the present invention.

FIG. 2 provides an example 200 of how image scanners may be grouped, according to some embodiments of the present invention. In this example, all scanners of a given type (e.g., software version, hardware capability, etc.) are grouped in to a single parent node in the software. Each individual scanner is then a child node of a parent node. Various linked data structures may be used to organize and link together the parent and child nodes using references (e.g., links or pointers). For example, in some embodiments, a linked list data structure is used where the parent node includes one or more references pointing to child nodes. In other embodiments, a tree data structure may be used with each parent node representing a tree and each child node representing a branch or leaf. This concept may be extended to have a tree for an organization (e.g., hospital) where each scanner type is a branch off the tree and each individual image scanner is a leaf off of a corresponding branch.

Continuing with reference to FIG. 2, a first type of scanner (referred to as "Type A" includes parent node 205A and a single child node 205B. Thus, there is only a single scanner of Type A known to the system. Conversely, a second type of scanner (referred to as "Type B") has a parent node 210A and two children nodes 210B and 210C which correspond to two physical scanners. This general grouping scheme may be extended to any number of scanners of a particular type. For example, there are three children nodes 215B, 215C, 215D under a parent node 215A for scanners of a third type of scanner (referred to as "Type C"). Thus, this grouping strategy may be scaled both up and down as the number of scanners in a particular organization increases or decreases, respectively. In some embodiments, each child node is configured to have an identical (actual or virtual) copy of the protocols on the parent node. Each time a new protocol is created on a child node (e.g., at a workstation associated with a particular image scanner), an administrator of the system 100 may be to be notified. The administrator then decides if this protocol needs to be disseminated to the other child nodes, within the same parent node or across other parent nodes. In some embodiments, an incremental archive is created for each parent node with the new protocol.

In some embodiments, each scanner holds a virtual copy of an imaging protocol stored on a centralized system such as the Protocol Database 140B. This virtual copy may be created, for example using symbolic link or "shortcut" functionality available in some operating systems. The use of a virtual copy allows the overall memory footprint associated with a protocol to be minimized. In one embodiment, any attempt by the user to modify the protocol causes a local copy of the protocol to be created at the scanner. The user may then send the updated protocol to the Protocol Management Computer 140A to notify an administrator of the system 100 of the change. Alternatively, the software associated with the scanner may automatically notify the system administrator upon detecting any changes to the virtual copy of a protocol.

Figure 3:
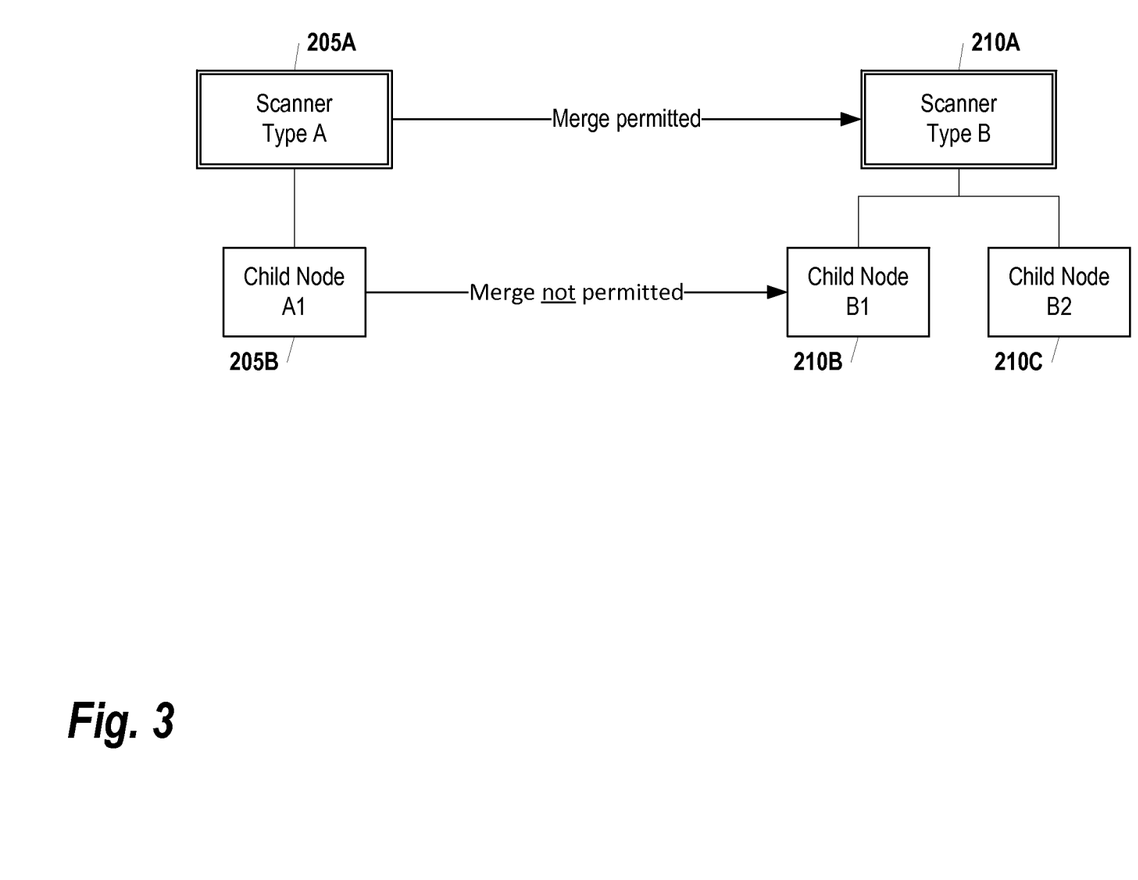
FIG. 3 provides a visualization of the rules for merging protocols across scanner types, according to some embodiments of the present invention.

FIG. 3 provides a visualization of the rules for merging protocols across scanner types, according to some embodiments of the present invention. In this example, there are two parent nodes 205A and 210A associated with scanners of Type A and Type B, respectively. Any merge of imaging protocols must occur between these parent nodes 205A and 210A. In some embodiments, when merging protocols across scanner types, the new protocol will first be converted to the recipient scanner type and then the administrator will be presented with the changes that arise as a result of the conversion. Then, the administrator may have an option to either accept the changes, reject the changes fully (in which case this protocol will not be available on that scanner type), or make additional changes that would make it acceptable. At the end of all conversion and merging operations, each scanner within the same parent node may then be upgraded to the new protocol by the parent node in the next refresh cycle. In some embodiments, the timing of this refresh cycle is predetermined by the administrator.

As shown in the example, of FIG. 3 merging of protocols can only occur at the parent nodes and not at the child nodes. This provides various benefits to protocol data security, consistency, and management. For example, with reference to FIG. 3, if child node 205B is allowed to transmit a protocol update to child node 210B, there is a risk that the protocol will be incompatible or otherwise suboptimal because the scanners associated with Nodes 205B and 210B are of different types. Moreover, any changes sent to child node 210B may not be further sent to child node 210C. This introduces inconsistency among different scanners of Type B.

Figure 4A:
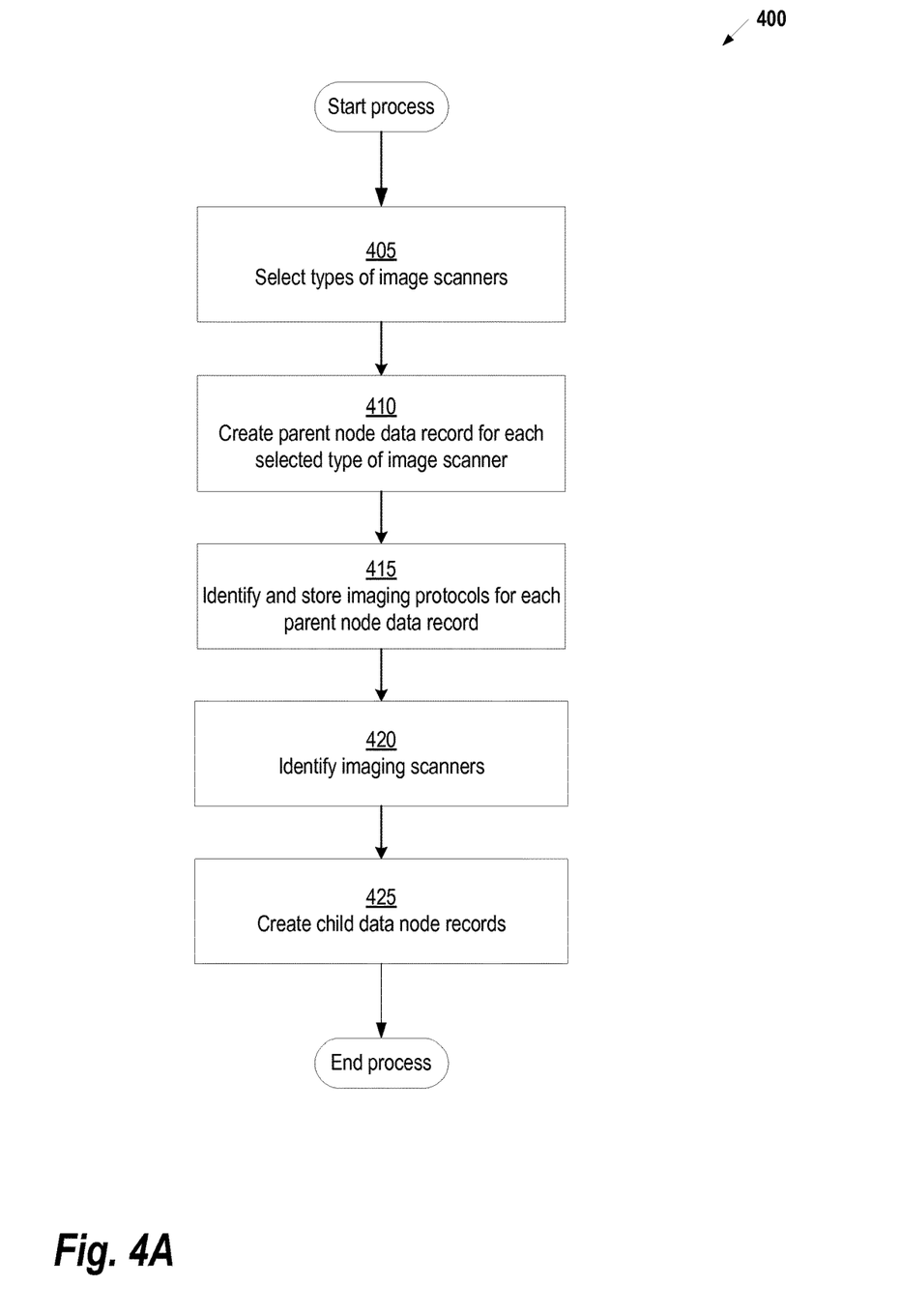
FIG. 4A describes a process for managing imaging protocols among a plurality of image scanners, according to some embodiments of the present invention.

FIG. 4A describes a process 400 for managing imaging protocols among a plurality of image scanners, according to some embodiments of the present invention. At 405 one or more types of image scanners are selected. This selection may occur automatically based on, for example, an identification of the types of image scanners available at a respective organization (e.g., hospital) or through retrieval of a listing of popular types of image scanners. Alternatively, in some embodiments, a user may select the types of scanners manually rather than using automatic selection. At 410, a parent node data record is created for each distinct type of image scanner selected at 405. Next, at 415, one or more standard imaging protocols are identified and stored for each of the parent node data records created at 410. The one or more standard imaging protocols stored for the parent are executable by any imaging scanner of the type corresponding to the parent. In some embodiments, each parent node data record is associated with a distinct imaging protocol. In some embodiments, the imaging protocol is stored directly in the parent node data record, while in other embodiments the parent node data record includes a reference (e.g., filename) to a file storing the imaging protocol information. Next, at 420, one or more actual image scanners are identified. Then, at 425 a process is executed to create a child node data record for each of the identified image scanners.

Figure 4B:
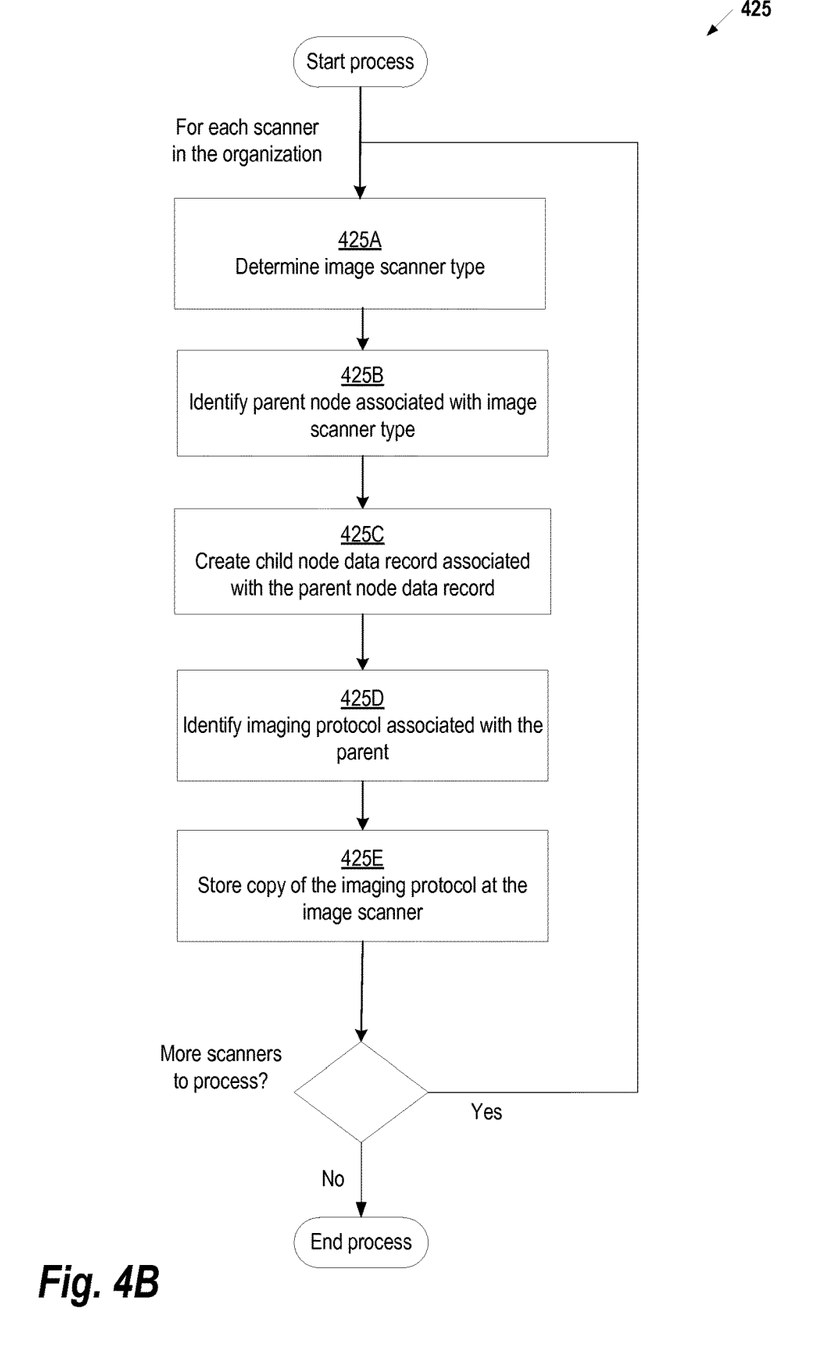
FIG. 4B describes the process of creating the child node data records, according to some embodiments of the present invention.

FIG. 4B provides additional detail of the process 425 of creating the child node data records, according to some embodiments of the present invention. This process executes in a loop over each image scanner identified at 420 in FIG. 4A. The process begins at 425A where the image scanner type of the respective image scanner is determined. This determination may be made, for example, by querying the image scanner itself for type information or information which can be used to derive the type information (e.g., model number). Alternatively, a user of the system may input the type information manually. Once the type information is determined, it is used at 425B to identify one of the parent node data records created at 410. If no parent node data record exists for the image scanner type, an error notification may be provided to an administrator of the system and/or a new parent node data record may be automatically created for the particular image scanner type.

The parent node data record identified at 425A is next used at 425C to create a child node data record associated with the particular parent node data record. The child node data record can include various information such as, without limitation, the model number of the corresponding image scanner, known users of the image scanner, and/or information about the location of the image scanner. The exact method of creating the child node data record at 425C can vary depending on how parent and child node data records are implemented in a particular embodiment. For example, in some embodiments, a tree data structure may be used with each parent node representing a tree and each child node data record representing a branch or leaf. In other embodiments, different data structures may be used. For example, in one embodiment, a parent node data record represents the head of a linked list and each child node data record is linked to its corresponding parent. Once the child node data record has been created, at 425D the imaging protocol associated with the parent is identified. Then, at 425E, a copy of the imaging protocol is stored at the corresponding imaging scanner. In some embodiments, rather than storing a full copy of the protocol, the scanner only saves a "virtual" copy which is linked to a master copy stored at the Protocol Management Computer 140A in association with the parent node data record.

Following the processes 400 and 425, any modifications to the imaging protocols may be managed at the parent node data record level. For example, in one embodiment, once a modification of a first imaging protocol is detected at an image scanner, the child node data record corresponding to that node is identified. This child node data record is used to identify the parent node data record which, in turn, is used to identify any additional child node data record linked to that parent (i.e., siblings of the child where the image protocol modification occurred). The modification of the image protocol can then be distributed to image scanners associated with the additional child node data records. The modification may also be stored at the Protocol Management Computer 140A in association with the parent node data record.

As discussed previously, in some embodiments, any modification of an imaging protocol cannot be transferred directly between child node data records. Rather, each change must be propagated up to the parent node data record and merged into another parent node data record. Thus, in some embodiments, following the process 400, the modified imaging protocol is merged into a second imaging protocol associated with a second parent node data record. This merging may entail, for example, a full conversion of the modified imaging protocol into the second imaging protocol or a replacement of one or more fields in the second imaging protocol. Once merge has been performed, the updated second imaging protocol is distributed to the imaging scanners corresponding to the child node data records linked to the second parent node data record. In one embodiment, an administrator may be notified prior to performing the distribution to the imaging scanners. The distribution may then be contingent upon receiving an approval message from the administrator. Moreover, this approval message may be a simple confirmation that the distribution may occur or, alternatively, the approval message may include additional modifications to be merged into the updated second imaging protocol prior to distribution to the image scanners.

Figure 5:
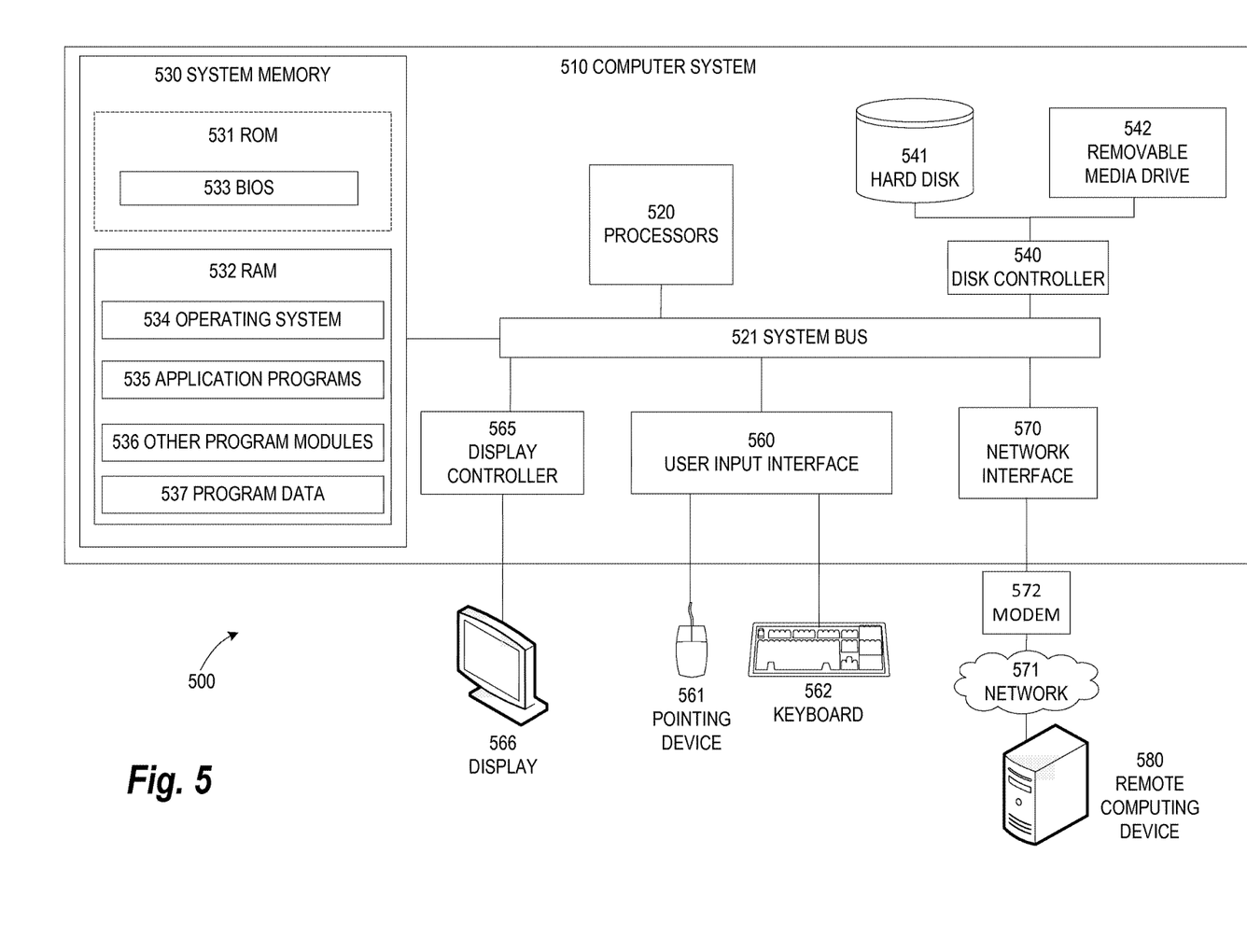
FIG. 5 illustrates an exemplary computing environment within which embodiments of the invention may be implemented.

FIG. 5 illustrates an exemplary computing environment 500 within which embodiments of the invention may be implemented. For example, computing environment 500 may be used to implement one or more components of system 100 shown in FIG. 1. Computers and computing environments, such as computer system 510 and computing environment 500, are known to those of ordinary skill in the art and thus are described briefly here.

As shown in FIG. 5, the computer system 510 may include a communication mechanism such as a system bus 521 or other communication mechanism for communicating information within the computer system 510. The computer system 510 further includes one or more processors 520 coupled with the system bus 521 for processing the information.

The processors 520 may include one or more central processing units (CPUs), graphical processing units (GPUs), or any other processor known in the art. More generally, a processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and be conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

Continuing with reference to FIG. 5, the computer system 510 also includes a system memory 530 coupled to the system bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system 533 (BIOS) containing the basic routines that help to transfer information between elements within computer system 510, such as during start-up, may be stored in system memory ROM 531. System memory RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the system bus 521 to control one or more storage devices for storing information and instructions, such as a magnetic hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the system bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the one or more processors 520. The pointing device 561, for example, may be a mouse, a light pen, a trackball, or a pointing stick for communicating direction information and command selections to the one or more processors 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the one or more processors 520 executing one or more sequences of one or more instructions contained in a memory, such as the system memory 530. Such instructions may be read into the system memory 530 from another computer readable medium, such as a magnetic hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hard-wired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the one or more processors 520 for execution. A computer readable medium may take many forms including, but not limited to, non-transitory, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the system bus 521. Transmission media may also take the form of acoustic or light waves, such as those generated during radio wave and infrared data communications. In some embodiments, the computer readable medium is part of an article of manufacture which may be distributed separately from the computer system 510 to allow for execution of the computer readable medium by other computer systems.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to system bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computing 580). The network 571 may be wired, wireless or a combination thereof. Wired connections may be implemented using Ethernet, Universal Serial Bus (USB), RJ-6, or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically, wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

I claim:

1. A computer-implemented method for managing imaging protocols among a plurality of image scanners, the method comprising:
   creating a plurality of parent node data records, each respective parent node data records corresponding to a distinct type of image scanner;
   storing, at a centralized database, a plurality of imaging protocols, each imaging protocol associated with a distinct parent node data record included in the plurality of parent node data records;
   performing a child node creation process for each respective image scanner included in the plurality of image scanners, the child node creation process comprising:
      determining a respective image scanner type associated with a respective image scanner,
      identifying a respective parent node data record corresponding to the respective image scanner type,
      creating a child node data record associated with the respective parent node data record,
      identifying a respective imaging protocol associated with the respective parent node data record, and
      storing a copy of the respective imaging protocol at the respective scanner, wherein the copy of the respective imaging protocol is a virtual copy linked to the respective imaging protocol stored at the centralized database;
   detecting a modification of a first imaging protocol at a first image scanner;
   identifying a first child node data record corresponding to the first image scanner;
   determining a first parent node data record associated with the first child node data record;
   determining one or more additional child node data records associated with the first parent node data record; and
   distributing the modification of the first imaging protocol to one or more additional image scanners associated with the one or more additional child node data records.

2. The method of claim 1, further comprising:
   storing the modification of the first imaging protocol with an association to the first parent node data record.

3. The method of claim 2, further comprising:
   identifying a second imaging protocol associated with a second parent node data record;
   merging the modification of the first imaging protocol into the second imaging protocol to yield an updated second imaging protocol;
   identifying one or more second child node data records associated with the second parent node data record;
   determining one or more second image scanners corresponding to the second child node data records; and
   distributing the updated second imaging protocol to the one or more second image scanners.

4. The method of claim 3, further comprising:

prior to distributing the updated second imaging protocol, providing a notification to an administrator describing the updated second imaging protocol.

5. The method of claim 4, wherein the updated second imaging protocol is only distributed to the one or more second image scanners if an approval is received from the administrator in response to the notification.

6. The method of claim 4, further comprising:
   receiving one or more additional modifications from the administrator in response to the notification; and
   merging the one or more additional modifications into the updated second imaging protocol prior to distributing the updated second imaging protocol to the one or more second image scanners.

7. The method of claim 2, further comprising:
   archiving the first imaging protocol prior to storing the modification of the first imaging protocol with the association to the first parent node data record.

8. An article of manufacture for managing imaging protocols among a plurality of image scanners, the article of manufacture comprising a non-transitory, tangible computer-readable medium holding computer-executable instructions for performing a method comprising:
   creating a plurality of parent node data records, each respective parent node data records corresponding to a distinct type of image scanner;
   storing, at a centralized database, a plurality of imaging protocols, each imaging protocol associated with a distinct parent node data record included in the plurality of parent node data records;
   performing a child node creation process for each respective image scanner included in the plurality of image scanners, the child node creation process comprising:
      determining a respective image scanner type associated with a respective image scanner,
      identifying a respective parent node data record corresponding to the respective image scanner type,
      creating a child node data record associated with the respective parent node data record,
      identifying a respective imaging protocol associated with the respective parent node data record, and
      storing a copy of the respective imaging protocol at the respective scanner, wherein the copy of the respective imaging protocol is a virtual copy linked to the respective imaging protocol stored at the centralized database;
   detecting a modification of a first imaging protocol at a first image scanner;
   identifying a first child node data record corresponding to the first image scanner;
   determining a first parent node data record associated with the first child node data record;
   determining one or more additional child node data records associated with the first parent node data record; and
   distributing the modification of the first imaging protocol to one or more additional image scanners associated with the one or more additional child node data records.

9. The article of manufacture of claim 8, wherein the method further comprises:
   identifying a second imaging protocol associated with a second parent node data record;
   merging the modification of the first imaging protocol into the second imaging protocol to yield an updated second imaging protocol;
   identifying one or more second child node data records associated with the second parent node data record;

determining one or more second image scanners corresponding to the second child node data records; and distributing the updated second imaging protocol to the one or more second image scanners.

10. The article of manufacture of claim 9, wherein the method further comprises:

prior to distributing the updated second imaging protocol, providing a notification to an administrator describing the updated second imaging protocol.

11. The article of manufacture of claim 10, wherein the method further comprises:

receiving one or more additional modifications from the administrator in response to the notification; and merging the one or more additional modifications into the updated second imaging protocol prior to distributing the updated second imaging protocol to the one or more second image scanners.

12. The article of manufacture of claim 8, wherein the method further comprises:

archiving the first imaging protocol; and storing the modification of the first imaging protocol with an association to the first parent node data record.

* * * * *